US00PP20993P2

(12) United States Plant Patent
Hartman

(10) Patent No.: US PP20,993 P2
(45) Date of Patent: May 11, 2010

(54) ***CALADIUM* PLANT NAMED 'ROSEMARY'**

(50) Latin Name: *Caladium×hortulanum*
Varietal Denomination: Rosemary

(76) Inventor: Robert Dale Hartman, 158 Blue Moon Ave., Lake Placid, FL (US) 33852

( * ) Notice: Subject to any disclaimer, the term of this patent is extended or adjusted under 35 U.S.C. 154(b) by 0 days.

(21) Appl. No.: 12/321,743

(22) Filed: Jan. 23, 2009

(51) Int. Cl.
*A01H 5/00* (2006.01)

(52) U.S. Cl. ..... Plt./373
(58) Field of Classification Search ..... Plt./373, Plt./263.1
See application file for complete search history.

*Primary Examiner*—Kent L Bell
(74) *Attorney, Agent, or Firm*—C. A. Whealy

(57) ABSTRACT

A new and distinct cultivar of *Caladium* plant named 'Rosemary', characterized by its intermediate plant habit; vigorous and dense growth habit; rapid growth rate; and strap-type leaves that are rose red in color in the center with mottled light and dark green-colored borders.

4 Drawing Sheets

Botanical designation: *Caladium×hortulanum.*
Cultivar denomination: 'ROSEMARY'.

BACKGROUND OF THE INVENTION

The present invention relates to a new and distinct cultivar of *Caladium* plant, botanically known as *Caladium×hortulanum*, commercially referred to as a strap leaf-type *Caladium* and hereinafter referred to by the name 'Rosemary'.

The objective of the Inventor's breeding program is to create new *Caladium* cultivars that have uniform plant habit, exceptional performance and attractive foliage coloration.

The new *Caladium* plant originated from a cross-pollination made by the Inventor in April, 2001, in Lake Placid, Fla. of *Caladium×hortulanum* 'White Wing', not patented, as the female, or seed, parent with *Caladium×hortulanum* 'Florida Red Ruffles', disclosed in U.S. Plant Pat. No. 13,136, as the male, or pollen, parent. The new *Caladium* plant was discovered and selected by the Inventor as a single plant within the progeny of the stated cross-pollination in a controlled outdoor nursery environment in Lake Placid, Fla. on Jun. 15, 2002.

Asexual reproduction of the new *Caladium* plant by tuber divisions in a controlled outdoor nursery environment in Lake Placid, Fla. since Apr. 15, 2003 has shown that the unique features of this new *Caladium* plant are stable and reproduced true to type in successive generations of asexual reproduction.

SUMMARY OF THE INVENTION

Plants of the new *Caladium* have not been observed under all possible environmental conditions. The phenotype may vary somewhat with variations in environment such as temperature and light intensity, without, however, any variance in genotype.

The following traits have been repeatedly observed and are determined to be the unique characteristics of 'Rosemary'. These characteristics in combination distinguish 'Rosemary' as a new and distinct cultivar of *Caladium:*

1. Intermediate plant habit.
2. Vigorous and dense growth habit; rapid growth rate.
3. Strap-type leaves that are rose red in color in the center with mottled light and dark green-colored borders.

Plants of the new *Caladium* differ from plants of the female parent, 'White Wing', in the following characteristics:

1. Plants of the new *Caladium* grow faster than plants of 'White Wing'.
2. Plants of the new *Caladium* and 'White Wing' differ in leaf coloration as plants of 'White Wing' have white-colored leaves with mottled dark and light green-colored borders.

Plants of the new *Caladium* differ from plants of the male parent, 'Florida Red Ruffles', in the following characteristics:

1. Plants of the new *Caladium* grow faster than plants of 'Florida Red Ruffles'.
2. Plants of the new *Caladium* are more upright than plants of 'Florida Red Ruffles'.
3. Plants of the new *Caladium* and 'Florida Red Ruffles' differ in leaf coloration as plants of 'Florida Red Ruffles' have red-colored leaves with green-colored borders.

Plants of the new *Caladium* can be compared to plants of 'Florida Sweetheart', disclosed in U. S. Plant Pat. No. 8,526. In side-by-side comparisons conducted in Lake Placid, Fla., plants of the new *Caladium* differed primarily from plants of 'Florida Sweetheart' in the following characteristics:

1 . Plants of the new *Caladium* were faster growing than plants of 'Florida Sweetheart'.
2. Plants of the new *Caladium* and 'Florida Sweetheart' differed in leaf coloration as plants of 'Florida Sweetheart' had pink-colored leaves with creamy white to green-colored borders.

Plants of the new *Caladium* can also be compared to plants of 'Red Frills', not patented. In side-by-side comparisons conducted in Lake Placid, Fla., plants of the new *Caladium* differed primarily from plants of 'Red Frills' in the following characteristics:

1. Plants of the new *Caladium* were more upright than plants of 'Red Frills'.
2. Leaves of plants of the new *Caladium* were more rounded than and not as pointed as leaves of plants of 'Red Frills'.
3. Plants of the new *Caladium* and 'Red Frills' differed in leaf coloration as plants of 'Red Frills' had red-colored leaves with dark green-colored borders.

BRIEF DESCRIPTION OF THE PHOTOGRAPHS

The accompanying photographs illustrate the overall appearance of the new *Caladium*. These photographs show the colors as true as it is reasonably possible to obtain in colored reproductions of this type. Colors in the photographs may differ slightly from the color values cited in the detailed botanical description which accurately describe the colors of the new *Caladium*.

The photograph on the first sheet is a side perspective view of a typical plant of 'Rosemary' grown in a container in a shadehouse.

The photograph at the top of the second sheet is a side perspective view of typical plants of 'Rosemary' (top center), 'Red Frills' (left) and 'Florida Sweetheart' (right) grown in a shadehouse.

The photograph at the bottom of the second sheet is a side perspective view of typical plants of 'Rosemary' (top center), 'White Wing' (left) and 'Florida Red Ruffles' (right) grown in a shadehouse.

The photograph at the top of the third sheet is a top perspective view of typical plants of 'Rosemary' grown in an outdoor nursery.

The photograph at the bottom of the third sheet is a close-up view of typical freshly-dug tubers and roots of 'Rosemary'.

The photograph on the fourth sheet is a close-up view of typical inflorescences of 'Rosemary'.

DETAILED BOTANICAL DESCRIPTION

The aforementioned photographs and following observations and measurements describe plants grown in 15-cm containers in Avon Park, Fla. during the spring in a polypropylene-covered shadehouse and plants grown in ground beds in Zolfo Springs, Fla. during the late summer in an outdoor nursery. All plants were grown under conditions and practices which approximate those generally used in commercial *Caladium* production. During the production of the plants, day temperatures ranged from about 29° C. to 35° C., night temperatures ranged from about 22° C. to 26° C. and light levels were about 8,000 foot-candles (shadehouse) or 10,000 to 12,000 foot-candles (outdoor nursery). Plants had been growing in the shadehouse for nine weeks from planting tubers when the photographs and the detailed description were taken. Plants had been growing in the outdoor nursery for seven months from planting tuber pieces when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Rosemary'.

Parentage:

*Female, or seed, parent.*—*Caladium×hortulanum* 'White Wing', not patented.

*Male, or pollen, parent.*—*Caladium×hortulanum* 'Florida Red Ruffles', disclosed in U.S. Plant Pat. No. 13,136.

Propagation:

*Type.*—By tubers and by tuber divisions.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented; individual segments oval to rounded in shape. Height: About 3.3 cm. Diameter: About 4.6 cm. Texture: Thick, starchy; somewhat brittle. Color: Epidermis, between 199D, 161D and 158B, with development, close to 200A to 200B; interior, between 155A to 2D. Root description: Dense, thick, fleshy; white, close to 155C, in color.

Plant description:

*Plant type.*—Herbaceous perennial.

*Plant/growth habit.*—Upright and intermediate plant habit; inverted triangle; rapid growth rate; vigorous, dense growth habit; suitable for 15-cm to 25-cm containers. Leaf petioles arising from tubers; petioles mostly upright and leaning outwardly with development.

*Plant height, from soil level to top of leaf plane, shadehouse-grown plants.*—About 23 cm to 27 cm.

*Plant height, from soil level to top of inflorescences, shadehouse-grown plants.*—About 31.5cm.

*Plant diameter or spread, shadehouse-grown plants.*—About 42 cm to 47 cm.

*Cataphylls* (*only observed on shadehouse-grown plants*).—Length: About 4 cm to 8 cm. Width: About 1.3 cm to 2 cm. Shape: Lanceolate. Apex: Acute. Base: Sheathing the stem. Color, inner and outer surfaces: Close to N170D tinged with close to 147A and variably streaked with close to 147C tinged with close to 200C; with development, color becoming closer to 200A to 200D and may be variably stained with close to 187A.

Foliage description:

*Length, shadehouse-grown plants.*—About 12.5 cm to 17.5 cm.

*Width, shadehouse-grown plants* (*flattened*).—About 7 cm to 11 cm.

*Shape.*—Ovate.

*Apex.*—Acuminate to acute.

*Base.*—Sagittate to cordate.

*Margin.*—Entire; undulate.

*Texture, upper surface.*—Smooth, glabrous.

*Texture, lower surface.*—Smooth, glabrous; glaucous.

*Venation pattern.*—Pinnate.

*Color, shadehouse-grown plants.*—Developing leaves, upper surface: Center: Close to 60B; towards the borders, sectors of N186C; basal notch, close to 60A. Border and margins: Mottled, close to 146C to 146D; or close to 146D tinged with close to N186C; or close to 147C to 147D; or close to 147C to 147D tinged with close to N186C; or between N189A to 147A. Venation: Midrib and lateral veins, close to 60A. Developing leaves, lower surface: Center: Close to 59D. Border and margins: Close to 148D or between 147B and N138B. Venation: Midrib, close to 181C to 181D; lateral veins, close to 182B to 182C. Fully expanded leaves, upper surface: Center: Close to 60B; towards the borders, sectors of N186C; basal notch, close to 60A. Border and margins: Mottled, between N189A and 147A with occasional flecking, close to 146C to 146D. Venation: Midrib and lateral veins, between 53A to 60A. Fully expanded leaves, lower surface: Center: Close to 59B to 59C; towards the borders, sectors of between 148A to 147A. Border and margins: Close to between 147A and N189B. Venation: Midrib, between 181C and 182B; lateral veins, close to 182B to 182C.

*Petiole.*—Aspect: Mostly erect, leaning outwardly with development. Length, shadehouse-grown plants: About 17.5 to 21 cm. Diameter, distal, shadehouse-grown plants: About 3 mm to 4 mm. Diameter, proximal, shadehouse-grown plants: About 6 mm to 9 mm. Color, proximal, shadehouse-grown plants: Close to N170D tinged with close to 147A and densely streaked with close to 200C tinged with close to 147A; variably and boldly striped with close to 200A. Color, distal, shadehouse-grown plants: Close to N170D tinged with close to 183D and 182D and densely streaked with close to 200C tinged with close to 147A; variably and boldly striped with close to 200A. Wing length, shadehouse-grown plants: About 4 cm to 8 cm. Wing diameter, shadehouse-grown plants: About 7 mm to 10 mm. Wing color, shadehouse-grown plants: Close to N170D tinged with close to 147A and variably streaked with 147C tinged with close to 200C.

Inflorescence description: Inflorescences only observed on shadehouse-grown plants.

*Inflorescence arrangement.*—Upright hooded spathes surrounding a columnar spadix borne on a tall upright scape. Spadix with sessile, simple female and male flowers separated into two zones. Female flowers arranged on the lower one-third of the spadix; male flowers arranged on the upper two-thirds of the spadix. Sterile flowers develop between female and male flower zones; near this area, the spathe constricts surrounding the female flowers.

*Fragrance.*—None detected.

*Natural flowering season/longevity.*—Plants of the new *Caladium* typically flower during the spring or early summer in central Florida. Flowers develop about eleven weeks after growth commences. Inflorescences last about three days before fading; inflorescences persistent.

*Spathe.*—Length: About 11 cm. Width, distal: About 3.6 cm. Width, proximal: About 2.2 cm. Width, at constriction: About 1.5 cm. Shape: Ovate to somewhat obovate. Apex: Acuminate. Base: Tapering. Margin: Entire; slightly reflexed. Texture, upper and lower surfaces: Smooth, glabrous. Color: Front surface: Upper two-thirds: Close to 159D tinged with close to 160D; color becoming closer to 199C to 199D with development. Lower one-third: Close to 148B to 148C tinged with close to 187A; color becoming closer to between 146B to 147B faintly mottled with close to 148C and faintly tinged with close to 181D with development. Rear surface: Upper two-thirds: Close to 160D tinged with close to 146D. Lower one-third: Between 146B and 147B faintly mottled with close to 148C and faintly tinged with close to 181D. Spadix: Length, entire spadix: About 6.8 cm. Length, male flower zone: About 5.5 cm. Length, sterile flower zone: About 9 mm. Length, female flower zone: About 1.8 cm. Diameter, male flower zone: About 9 mm. Diameter, sterile flower zone: About 6 mm. Diameter, female flower zone: About 9 mm. Shape: Spindle-shaped to columnar. Apex: Bluntly acute. Base: Obtuse. Aspect: Upright. Color, mature, male zone: Close to 158C tinged with close to 145C. Color, mature, sterile zone: Close to 158C tinged with close to 145C. Color, mature, female zone: Close to 13D. Male flowers: Quantity per spadix: About 120. Shape: Obovate. Height: About 3 mm. Diameter: About 3 mm. Anther color: Close to 158C. Amount of pollen: None observed. Female flowers: Quantity per spadix: About 165. Shape: Obovate. Height: About 3 mm. Diameter: About 2 mm. Stigma color: Close to 13D. Ovary color: Close to 155D. Scape: Length: About 20.5 cm. Diameter: About 5.5 mm. Strength: Sturdy; flexible. Aspect: Erect. Texture: Smooth, glabrous; glaucous. Color: Proximal: Close to N170D tinged with close to 147A, densely streaked with close to 200C tinged with close to 147A and variably striped with close to 200A. Distal: Close to N170D tinged with close to between 183D and 182D, densely streaked with close to 200C tinged with close to 147A and variably striped with close to 200A. Seed and fruit: Seed and fruit development have not been observed on plants of the new *Caladium.*

Disease/pest resistance: Plants of the new *Caladium* have been observed to be somewhat tolerant to *Pythium* root rot and *Xanthomonas* leaf spot. Plants of the new *Caladium* have not been observed to be resistant to pests or other pathogens common to *Caladium.*

Temperature tolerance: Plants of the new *Caladium* have been observed to be tolerant to temperatures ranging from about 7° C. to about 40° C.

It is claimed:

1. A new and distinct *Caladium* plant named 'Rosemary' as illustrated and described.

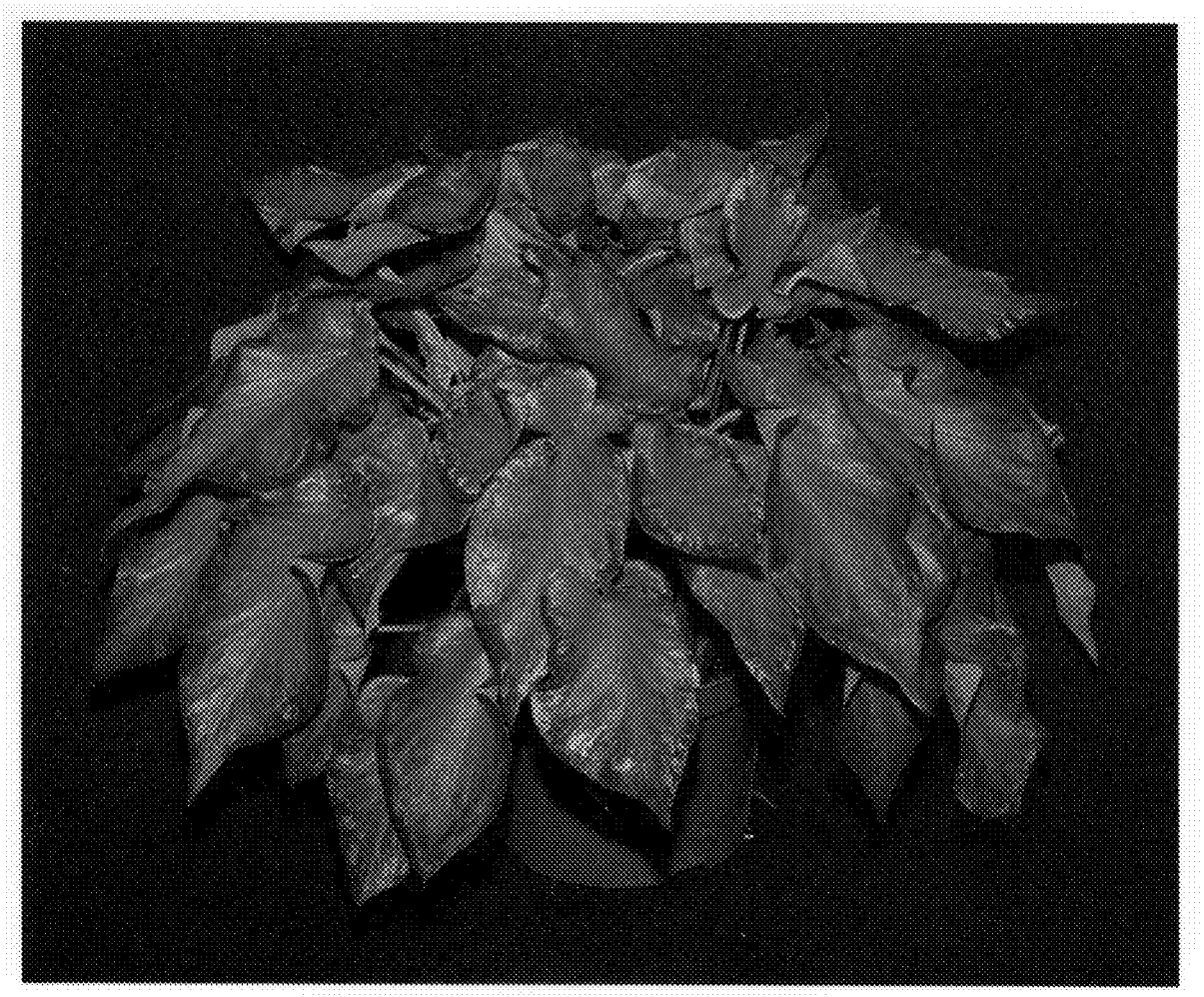

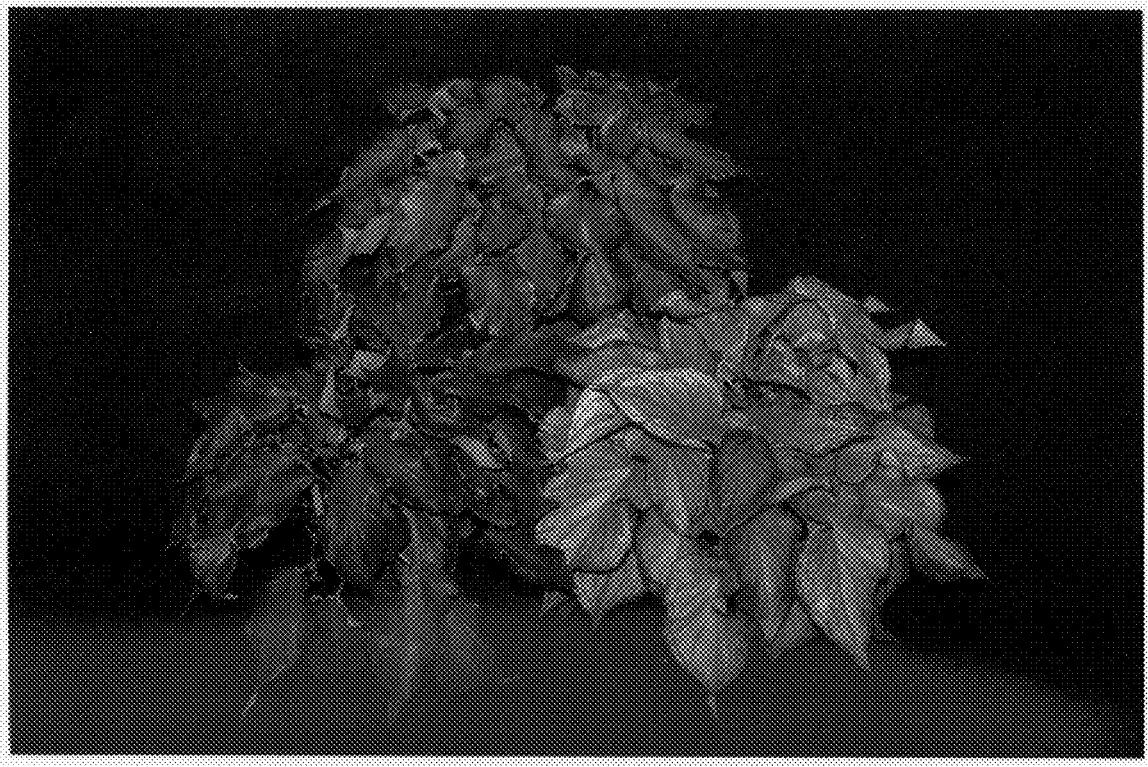
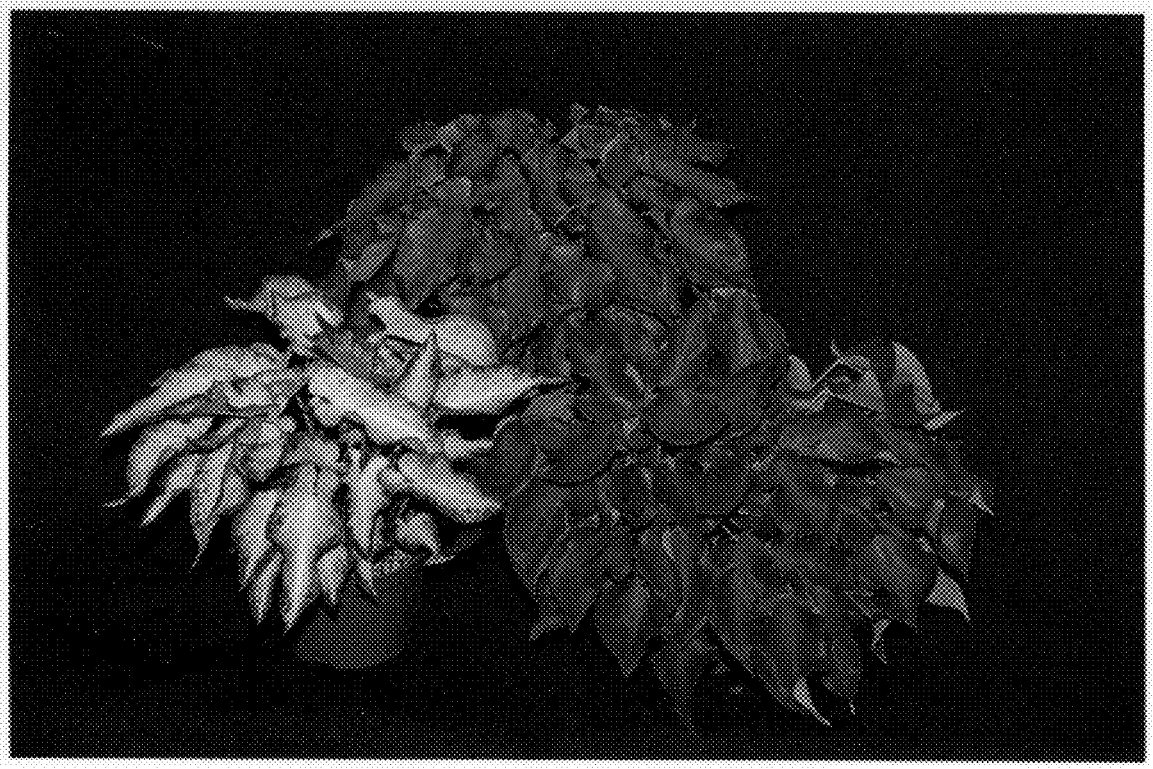

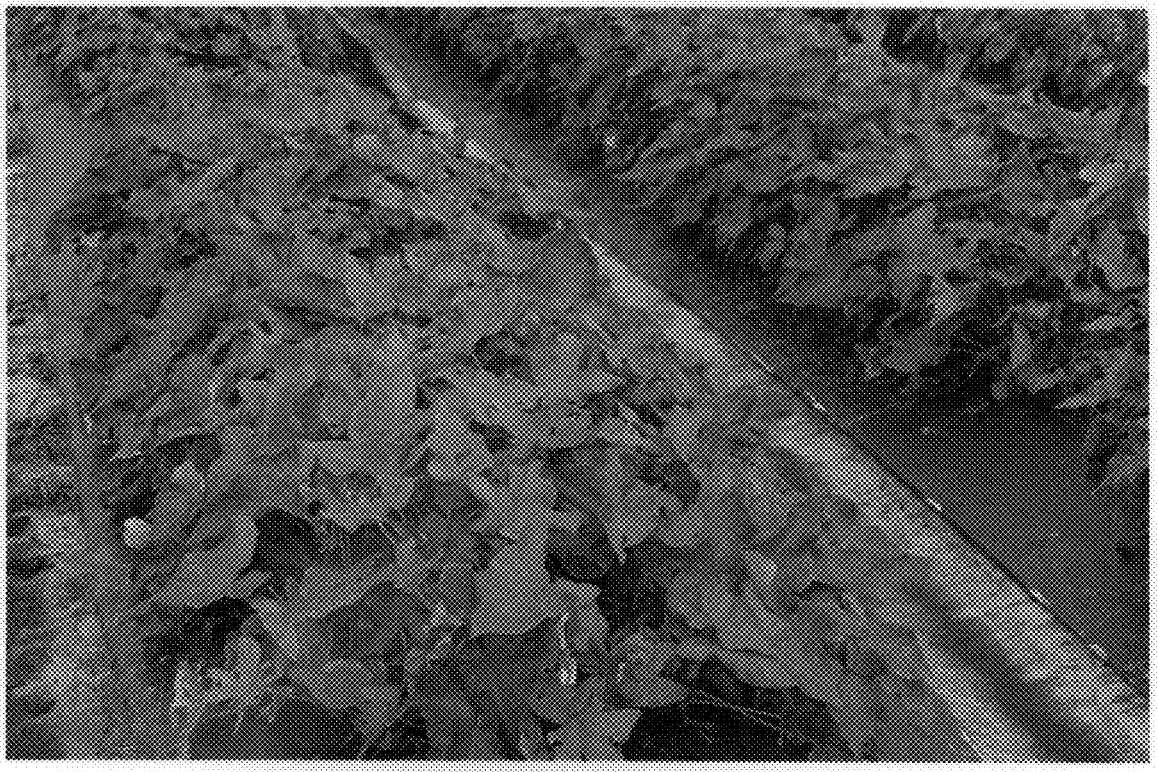
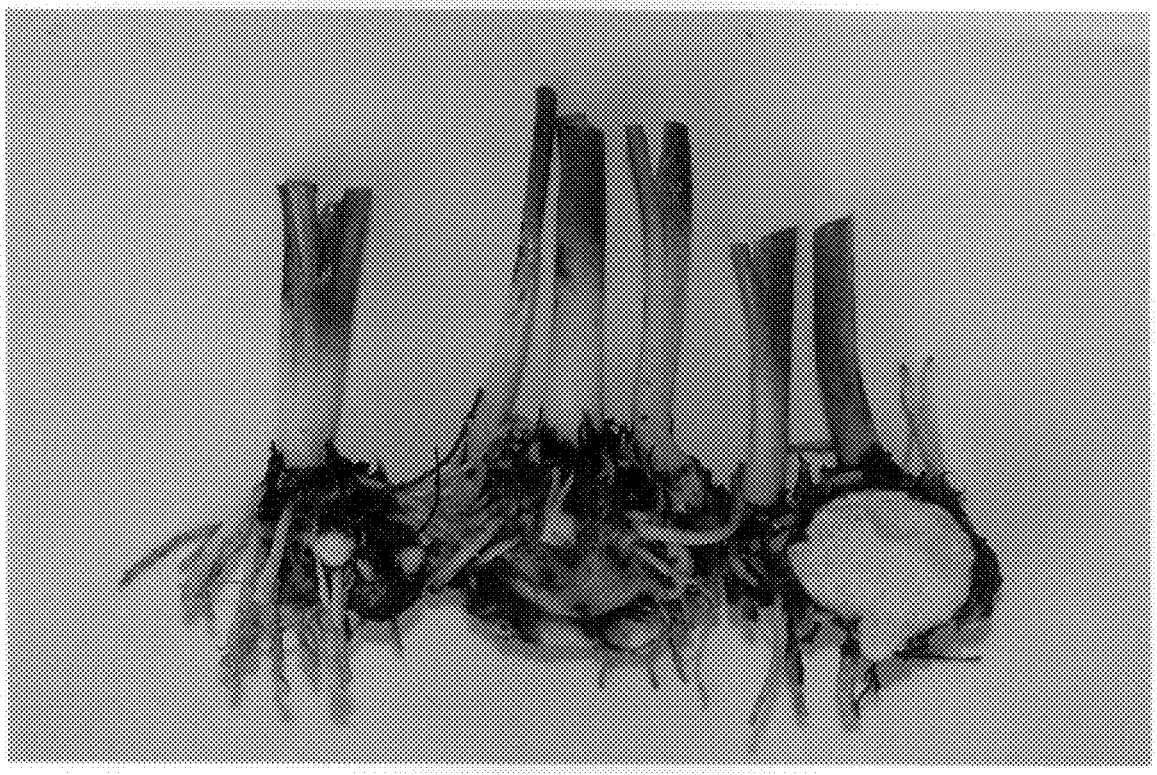

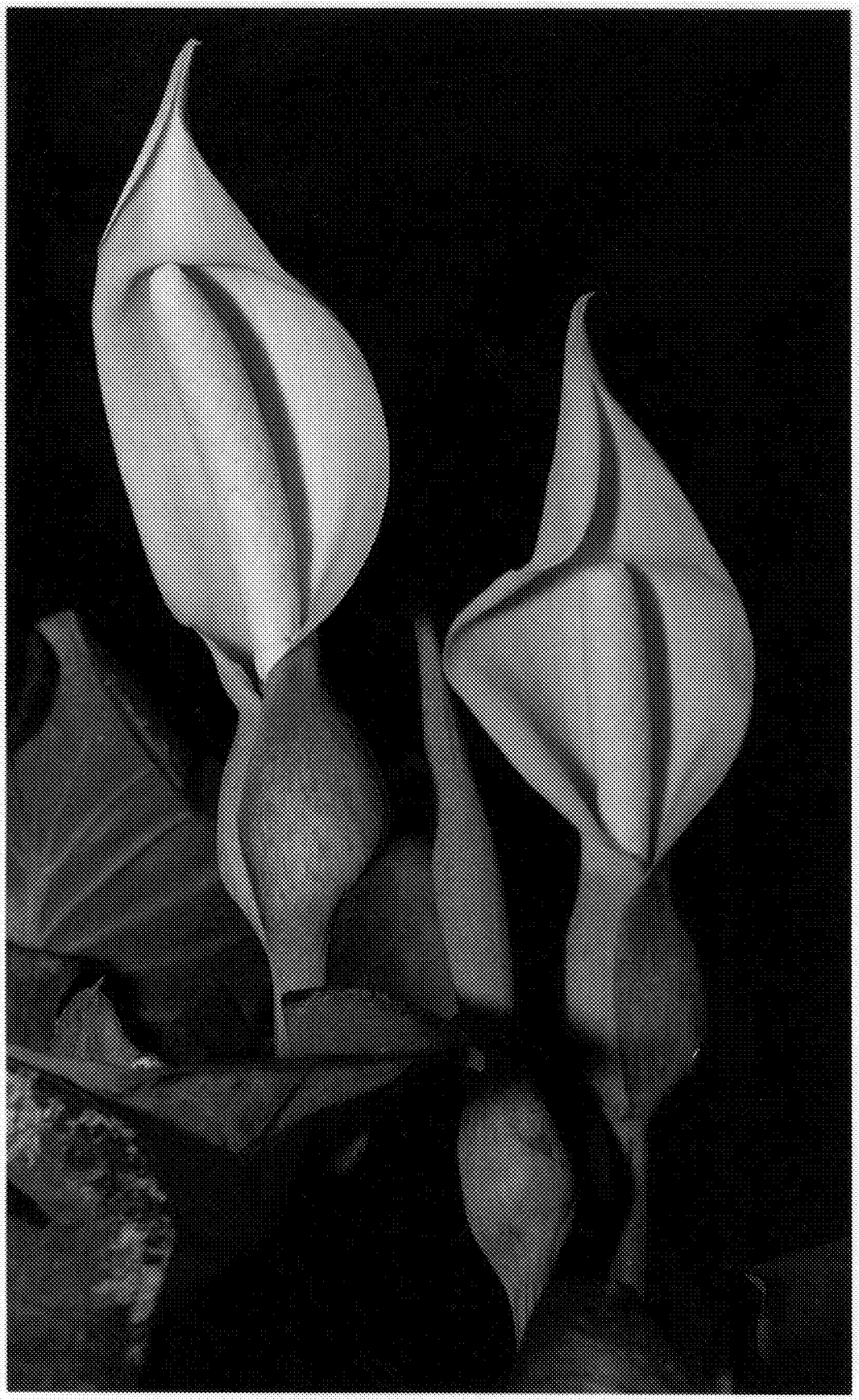

* * * * *